United States Patent
Balakrishnan

(10) Patent No.: US 8,086,413 B2
(45) Date of Patent: Dec. 27, 2011

(54) DISULPHIDE BOND CONNECTIVITY IN PROTEIN

(75) Inventor: Raju Balakrishnan, Karnataka (IN)

(73) Assignee: International Business Machines Corporation, Armonk, NY (US)

( * ) Notice: Subject to any disclaimer, the term of this patent is extended or adjusted under 35 U.S.C. 154(b) by 120 days.

(21) Appl. No.: 12/712,251

(22) Filed: Feb. 25, 2010

(65) Prior Publication Data

US 2010/0153020 A1    Jun. 17, 2010

Related U.S. Application Data

(62) Division of application No. 11/169,045, filed on Jun. 28, 2005, now Pat. No. 7,672,788.

(51) Int. Cl.
*G01N 33/00* (2006.01)
*G01N 33/68* (2006.01)
*G06F 15/00* (2006.01)

(52) U.S. Cl. .......................................... 702/19; 702/27

(58) Field of Classification Search .................. None
See application file for complete search history.

(56) References Cited

U.S. PATENT DOCUMENTS

| | | | |
|---|---|---|---|
| 5,265,030 A | 11/1993 | Skolnick et al. | |
| 5,436,850 A | 7/1995 | Eisenberg et al. | |
| 5,958,784 A | 9/1999 | Benner | |
| 2003/0187587 A1 | 10/2003 | Swindells et al. | |
| 2004/0148105 A1 | 7/2004 | Ondrechen et al. | |

OTHER PUBLICATIONS

Notice of Allowance (Mail Date Sep. 9, 2009) and Supplemental Notice of Allowability (Mail Date Jan. 26, 2010) for U.S. Appl. No. 11/169,045, Filing Date Jun. 28, 2005; Confirmation No. 2124.
Casadio et al.; A neural network-based method for predicting the disulfide connectivity in proteins; Biocomputing Unit and Lab of Biophysics, Dept. of Biology University of Bologna via Irnerio 42, 40126 Bologna Italy. 2004. 5 pages.
Frasconi et al.; A Two-Stage SVM Architecture for Predicting the Disulfide Bonding State of Cysteines; Dipartimento di Sistemi e Informatica, Universita di Firenze, Italy. 2001. 10 pages.
Gabow, Harold N.; An Efficient Implementation of Edmonds' Algorithm for Maximum Matching on Graphs; Journal of the Association for Computing machinery, vol. 23, No. 2, Apr. 1976; pp. 221-234.
Fariselli et al.; Prediction of disulfide connectivity in proteins; Oxford University Press 2001; Bioinformatics; vol. 17, No. 10; 2001; pp. 957-964.
Balakrishnan, Raju; Disulfide Connectivity Prediction in Proteins Based on Secondary Structures and Cysteine Separation; IBM Global Services India Pvt Ltd; Jun. 20, 2005; pp. 1-9.

*Primary Examiner* — Michael Borin
(74) *Attorney, Agent, or Firm* — Schmeiser, Olsen & Watts; John Pivnichny

(57) ABSTRACT

A method, computer system, and computer program product for determining N disulphide bond connections in a protein having 2N bonded sulphur atoms. Each sulphur atom is available for forming the N disulphide bond connections through use of an undirected graph having the 2N sulphur atoms as nodes and having an edge connecting each pair of nodes. Each sulphur atom is comprised by a cysteine of the protein. The cysteines are sequenced along a chain in the protein as ordered list of position indexes. A weight W of each edge between cysteine position indexes $I_1$ and $I_2$ is calculated as decreasing with increasing separation d between $I_1$ and $I_2$, wherein d is $|I_1 - I_2|/100$. The N disulphide bond connections are determined by optimizing an objective function formed from the calculated weights W.

13 Claims, 8 Drawing Sheets

|   | A | C | D | E | F | G | H | I | K | L | M |
|---|---|---|---|---|---|---|---|---|---|---|---|
| A | 1.077/ 0.901 | 0.892 | 1.073 | 1.064 | 1.155 | 1.111 | 1.097 | 1.018 | 1.143 | 1.244 | 1.344 |
| C | 0.901 | 0.566/ 0.564 | 0.807 | 0.765 | 0.619 | 0.798 | 0.949 | 0.757 | 0.971 | 0.811 | 0.570 |
| D | 0.952 | 1.526 | 1.028/ 0.936 | 0.876 | 0.828 | 0.889 | 0.716 | 0.990 | 0.858 | 1.054 | 1.205 |
| E | 1.089 | 1.238 | 1.089 | 0.998/ 1.010 | 1.034 | 0.944 | 0.539 | 0.945 | 1.007 | 1.171 | 1.193 |
| F | 1.153 | 0.625 | 0.833 | 1.232 | 1.195/ 1.295 | 0.783 | 0.962 | 0.787 | 0.959 | 1.308 | 1.359 |
| G | 0.909 | 1.103 | 0.877 | 1.046 | 0.893 | 1.304/ 1.308 | 1.433 | 0.845 | 0.877 | 1.013 | 0.856 |
| H | 1.213 | 1.367 | 0.716 | 1.049 | 0.955 | 0.919 | 1.568/ 1.566 | 0.870 | 0.764 | 1.336 | 1.164 |
| I | 1.011 | 1.166 | 0.982 | 0.750 | 1.090 | 0.845 | 1.252 | 0.992/ 0.799 | 0.948 | 1.132 | 1.277 |
| K | 1.146 | 0.963 | 1.036 | 0.918 | 1.070 | 0.859 | 1.168 | 1.049 | 1.017/ 1.016 | 1.144 | 0.880 |
| L | 1.359 | 1.217 | 1.035 | 1.258 | 1.316 | 1.097 | 1.344 | 1.108 | 1.255 | 1.233/ 1.293 | 0.781 |
| M | 0.961 | 0.558 | 1.103 | 1.174 | 1.170 | 0.735 | 1.130 | 0.783 | 0.854 | 0.857 | 0.715/ 0.713 |
| N | 0.985 | 1.191 | 0.956 | 1.045 | 1.080 | 0.811 | 1.295 | 0.939 | 0.934 | 0.948 | 0.701 |
| P | 0.902 | 0.907 | 0.870 | 1.048 | 1.273 | 1.047 | 0.710 | 0.980 | 1.028 | 0.942 | 0.793 |
| Q | 0.988 | 1.202 | 1.266 | 1.125 | 1.297 | 1.047 | 1.235 | 0.746 | 1.292 | 1.240 | 0.917 |
| R | 0.989 | 0.756 | 0.810 | 1.097 | 1.187 | 0.970 | 1.006 | 0.706 | 0.895 | 1.112 | 0.948 |
| S | 0.901 | 1.180 | 1.104 | 1.055 | 0.930 | 1.087 | 1.053 | 1.068 | 1.048 | 1.038 | 1.160 |
| T | 1.095 | 0.911 | 1.065 | 1.026 | 0.893 | 0.939 | 1.053 | 0.919 | 0.903 | 1.218 | 1.002 |
| V | 0.958 | 0.839 | 1.016 | 1.039 | 1.057 | 0.954 | 1.113 | 0.733 | 1.131 | 1.079 | 0.992 |
| W | 0.980 | 0.899 | 0.932 | 0.921 | 1.123 | 0.937 | 1.988 | 0.780 | 0.708 | 0.725 | 0.932 |
| Y | 1.157 | 0.607 | 0.997 | 1.248 | 1.080 | 0.938 | 1.512 | 0.849 | 0.952 | 0.972 | 0.989 |

DISULPHIDE BOND CONNECTIVITY IN PROTEIN

This application is a divisional application claiming priority to Ser. No. 11/169,045, filed Jun. 28, 2005.

BACKGROUND OF THE INVENTION

1. Technical Field

The present invention relates to a method, computer system, and computer program product for determining disulphide bond connectivity in protein.

2. Related Art

Fariselli and Casadio approached problem of predicting disulphide connectivity by equating the problem to a maximum graph matching problem and assigning edge weights based on the residues in the nearest neighborhood of the cysteines. Weights derived by monte carlo simulated annealing in combination with Edmond-Gabow maximum weighted graph matching algorithm was found to be giving best prediction accuracies for Fariselli and Casadio. See Piero Fariselli and Rita Casadio, "Prediction of disulphide connectivity to proteins", BioInformatics, Vol 17 No. 10 (2001).

In addition, neural network methods have been used to determine the disulphide bond connectivity of protein. However, a neural network method has the disadvantage of requiring time and effort to train data, and the accuracy the determination of disulphide connectivity of proteins depends on the amount and quality of the data that is trained. Thus, there is a need for a method for determining disulphide bond connectivity in protein that is capable of achieving high accuracy without a need to train data.

SUMMARY OF THE INVENTION

The present invention provides a method for determining N disulphide bond connections in a protein comprising 2N bonded sulphur atoms, each sulphur atom of the N sulphur atoms being available for forming the N disulphide bond connections through use of an undirected graph having the 2N sulphur atoms as nodes and having an edge connecting each pair of nodes of the N nodes, each edge being a potential disulphide bond connection of the N disulphide bond connections to be determined, each sulphur atom of the 2N sulphur atoms being independently comprised by a cysteine of the protein, said cysteines being sequenced along a chain in the protein in accordance with an ordered list of position indexes 0, 1, 2, . . . , said N at least 2, said method comprising:

for each edge between a first sulphur atom $S_1$ of a cysteine positioned at a position index $I_1$ of the chain and a second sulphur atom $S_2$ of a cysteine positioned at a position index $I_2$ of the chain: calculating a weight W of each edge in proportion to $W_d$, said $W_d$ decreasing with increasing separation d between $I_1$ and $I_2$, said d being defined as $|I_1-I_2|/100$; and determining the N disulphide bond connections subject to optimizing an objective function formed from the calculated edge weights W.

The present invention provides a computer system comprising a processor and a computer readable memory unit coupled to the processor, said memory unit containing instructions that when executed by the processor implement a method for determining N disulphide bond connections in a protein comprising 2N bonded sulphur atoms, each sulphur atom of the N sulphur atoms being available for forming the N disulphide bond connections through use of an undirected graph having the 2N sulphur atoms as nodes and having an edge connecting each pair of nodes of the N nodes, each edge

2 being a potential disulphide bond connection of the N disulphide bond connections to be determined, each sulphur atom of the 2N sulphur atoms being independently comprised by a cysteine of the protein, said cysteines being sequenced along a chain in the protein in accordance with an ordered list of position indexes 0, 1, 2, . . . , said N at least 2, said method comprising:

for each edge between a first sulphur atom $S_1$ of a cysteine positioned at a position index $I_1$ of the chain and a second sulphur atom $S_2$ of a cysteine positioned at a position index $I_2$ of the chain: calculating a weight W of each edge in proportion to $W_d$, said $W_d$ decreasing with increasing separation d between $I_1$ and $I_2$, said d being defined as $|I_1-I_2|/100$; and determining the N disulphide bond connections subject to optimizing an objective function formed from the calculated edge weights W.

The present invention provides a computer program product, comprising a computer usable medium having a computer readable program code embodied therein, said computer readable program code comprising an algorithm adapted to implement a method for determining N disulphide bond connections in a protein comprising 2N bonded sulphur atoms, each sulphur atom of the N sulphur atoms being available for forming the N disulphide bond connections through use of an undirected graph having the 2N sulphur atoms as nodes and having an edge connecting each pair of nodes of the N nodes, each edge being a potential disulphide bond connection of the N disulphide bond connections to be determined, each sulphur atom of the 2N sulphur atoms being independently comprised by a cysteine of the protein, said cysteines being sequenced along a chain in the protein in accordance with an ordered list of position indexes 0, 1, 2, . . . , said N at least 2, said method comprising:

for each edge between a first sulphur atom $S_1$ of a cysteine positioned at a position index $I_1$ of the chain and a second sulphur atom $S_2$ of a cysteine positioned at a position index $I_2$ of the chain: calculating a weight W of each edge in proportion to $W_d$, said $W_d$ decreasing with increasing separation d between $I_1$ and $I_2$, said d being defined as $|I_1-I_2|/100$; and determining the N disulphide bond connections subject to optimizing an objective function formed from the calculated edge weights W.

The present invention provides a process for integrating computing infrastructure, said process comprising integrating computer-readable code into a computing system, wherein the code in combination with the computing system is capable of performing a method for determining N disulphide bond connections in a protein comprising 2N bonded sulphur atoms, each sulphur atom of the N sulphur atoms being available for forming the N disulphide bond connections through use of an undirected graph having the 2N sulphur atoms as nodes and having an edge connecting each pair of nodes of the N nodes, each edge being a potential disulphide bond connection of the N disulphide bond connections to be determined, each sulphur atom of the 2N sulphur atoms being independently comprised by a cysteine of the protein, said cysteines being sequenced along a chain in the protein in accordance with an ordered list of position indexes 0, 1, 2, . . . , said N at least 2, said method comprising:

for each edge between a first sulphur atom $S_1$ of a cysteine positioned at a position index $I_1$ of the chain and a second sulphur atom $S_2$ of a cysteine positioned at a position index $I_2$ of the chain: calculating a weight W of each edge in proportion to $W_d$, said $W_d$ decreasing with increasing separation d between $I_1$ and $I_2$, said d being defined as $|I_1-I_2|/100$; and determining the N disulphide bond connections subject to optimizing an objective function formed from the calculated edge weights W.

The present invention advantageously provides a need for a method for determining disulphide bond connectivity in protein that is capable of achieving high accuracy without a need to train data.

BRIEF DESCRIPTION OF THE DRAWINGS

FIG. 3 depicts Monte Carlo calculated contact potentials, in accordance with the related art.

DETAILED DESCRIPTION OF THE INVENTION

Proteins, the building blocks of life, comprise chains of amino acids. There are 20 different types of amino acids comprised by proteins. A protein may have a single chain of amino acids or may have multiple amino acid chains linked together.

Protein structure may be viewed in four levels, namely, primary, secondary, tertiary and quaternary levels. The primary structure of a protein pertains to the type and sequence of amino acids linked together in chains. The secondary structure of a protein pertains to a local conformation of a segment of a chain and may represent strands formed by the local bending of amino acids (e.g., alpha ($\alpha$) helix, beta ($\beta$) sheet, random coil). The tertiary structure of a protein pertains to a three dimensional structure of a chain in which the secondary structures become tangled in different shapes (e.g. fibrous, globular). The quaternary structure refers to the manner in which different chains in the protein are bonded together.

The present invention relates to determining the tertiary structure of proteins, which is important in medical science. Given the primary structure, an accurate determination of tertiary structure can avoid the cost of an experimental determination of the tertiary structure, and may also facilitate the detection of tertiary structures of many proteins for which empirical detection is difficult or not possible.

Figure 1:
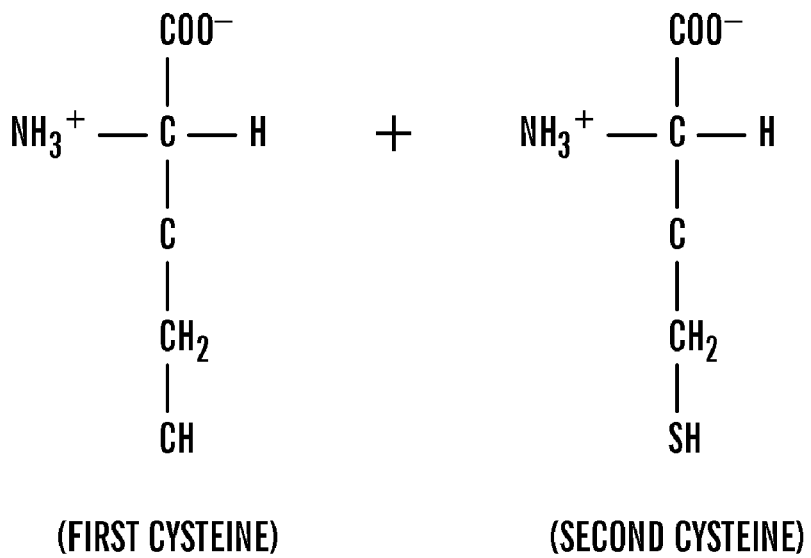
FIG. 1 depicts a disulphide bond in a reaction product formed from oxidation of a first cysteine and a second cysteine, in accordance with the related art.
Figure 1:
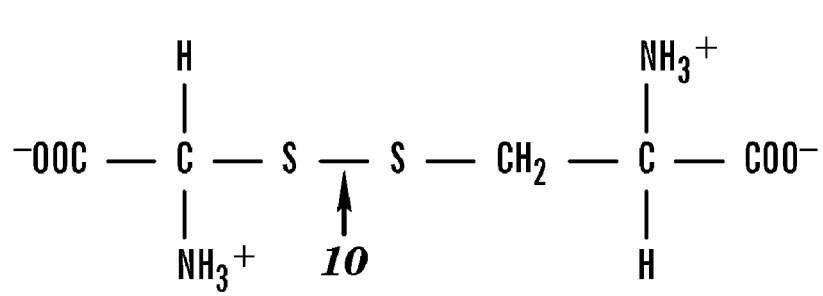

A disulphide bond in a protein is a sulphur-sulphur (S—S) bond formed between two sulfur atoms in a protein. FIG. 1 depicts a disulphide bond 10 in a reaction product formed from oxidation of a first cysteine and a second cysteine. In FIG. 1, the phrase "$H_2$ (OXIDATION)" denotes that the chemical reaction results in removal of hydrogen ($H_2$).

Unless otherwise stated, the term "bond" means "disulphide bond" herein, and a bond between two cysteines means a bond between sulphur atoms of the respective two cysteines.

Cysteine is the only residue forming disulphide bonds. The major type of forces contributing to the protein folding comprise disulphide bonds and hydrogen bonds. In a protein, there are much fewer disulphide bonds than hydrogen bonds, but the disulphide bonds are much stronger than the hydrogen bonds. Therefore, it is simpler to determine disulphide bonds than to determine hydrogen bonds. Also, the disulphide bonds can act as a test area for hypothesis regarding protein folding. Formation of the disulphide bonds adds to the stability of the protein conformations. Accurate determination of disulphide bonds will help tertiary structure determination of proteins considerably, by reducing the conformational search space for the three dimensional tertiary structure.

Determination of disulphide bonds involves two sub-problems. The first sub-problem is to determine the bonding state of cysteines (i.e., which cysteines in a protein are bonded and which cysteines are unbonded). The second sub-problem is the determination of the connectivity of cysteines (i.e., determination of which sulphur atoms in a protein are bonded together in the disulphide bonds). There are good solutions available for first sub-problem. Also in a protein chain bonded and un-bonded cysteines rarely co-exist. The present invention focuses on the second sub-problem, namely determining the disulphide bond connectivity.

Given primary structure (i.e., the amino acid sequence) and secondary structure information of a protein chain having 2N bonded cysteines and N associated disulphide bonds to be determined, the present invention determines the bonding pattern of the N disulphide bonds in the protein. In other words, given all disulphide bonds that are logically possible, the present invention determines which of these logically possible disulphide bonds are actually formed in the protein.

The difficulty for determining disulphide bond connectivity in a protein increases with increasing number of disulphide bonds in the protein. Therefore, the accuracy of the determination should be evaluated against the number of cysteines in the proteins chain. For example for a protein with only two cysteines and one disulphide bridge, the accuracy for determination will be always 100%, since there is only one disulphide bonding possible. For a chain with four cysteines, however, the accuracy of a random predictor is 50%. Thus, as the number of disulphide bonds increases, the probability of a correct determination by the random predictor also decreases.

Accuracy results for the methodology of the present invention are presented infra in Table 2 using a data set comprising proteins having 2 to 6 disulphide bonds. The Swiss-Prot database was searched, using the "Swiss-Prot Protein knowledgebase" website, for all the proteins having the disulphide bonds (i.e., proteins using the string DISULFID) and the resultant proteins were downloaded. Then proteins with more than one chain and with un-bonded cysteines were removed from the downloaded proteins. In addition, proteins with disulphide bonds of type "POTENTIAL, PROBABLE, BY SIMILARITY and REDOX ACTIVE" and ambiguous residue names (e.g., "X") were next removed from the downloaded proteins.

The present invention does not require that all cysteines in the protein be bonded, but rather performs the connectivity calculations for only those cysteines in the protein which are assumed to be bonded.

The present invention models the cysteines in the protein as a single chain. Therefore, multiple chains are represented as a single chain.

The present invention utilizes the primary structure (i.e., the amino acid sequence) and secondary structure information of a protein chain as input.

Two measures of accuracy of the connectivity determination are used herein. The first measure is the fraction of bonds determined correctly (Qc). The second measure of accuracy is the fraction of proteins for which all the bonds are determined correctly (Qp). More specifically:

Qc=number of bonds determined correctly/total number of possible bonds;

Qp=number of proteins having all bonds determined correctly/total number of proteins.

For a random predictor the measures for accuracy are:

$$Q_c \text{ for Random Predictor: } Q_c(R_p) = \frac{1}{2B-1} \quad (1)$$

$$Q_p \text{ for Random Predictor: } Q_p(R_p) = \frac{1}{(2B-1)!!} \quad (2)$$

$$= \frac{1}{\prod_{i \le B}(2i-1)}$$

where B is the number of disulphide bonds in the protein. See Piero Fariselli and Rita Casadio, "Prediction of disulphide connectivity to proteins", BioInformatics, Vol 17 No. 10 (2001).

The disulphide connectivity pattern may be viewed as a undirected graph, with nodes as cysteines and edges as bonding between the cysteines. The weights for the graph edges are assigned by methods described infra. An objective function formed from the assigned weights is then used find out an optimal connectivity (i.e., an optimal set of bonded sulphur pairs (i.e., disulphides)). For example, the objective function may be the sum of the edge weights of the N disulphide bonds, and the Edmond-Gabow (EG) N-cubed maximum weighted matching algorithm for undirected graphs may be used to find the optimal connectivity. The EG algorithm determines the set of bonded sulphur pairs (i.e., disulphides) for which the objective function (i.e., the sum of the weights of the N disulphide bonds) is a maximum.

Bonding between cysteines means bonding between sulphur atoms of the respective cysteines. Thus, the nodes are at the sulphur atoms in the respective cysteines, and the edges represent bonds connecting the sulphur atoms in the respective cysteines.

For example, consider a protein with 6 bonded cysteines denoted as C1, C2, ..., C6. Next, weights are assigned to the edges between the sulphur atoms of the cysteines pairs as shown in the symmetric matrix of Table 1.

TABLE 1

|    | C1 | C2 | C3 | C4 | C5 | C6 |
|----|----|----|----|----|----|----|
| C1 | —  | 2  | 6  | 5  | 7  | 4  |
| C2 | 2  | —  | 6  | 7  | 1  | -1 |
| C3 | 6  | 6  | —  | 6  | 8  | 3  |
| C4 | 5  | 7  | 6  | —  | 6  | 8  |
| C5 | 7  | 1  | 8  | 6  | —  | 1  |
| C6 | 4  | -1 | 3  | 8  | 1  | —  |

Although the edge weights in Table 1 are shown as integers, generally the edge weights are real numbers which may comprise integers.

Once the weights for the graph edges are assigned, the problem is to determine 3 pairs of cysteines in Table 1 which maximize the sum of the weights, which is an optimization problem. For performing said maximizing of the weights, the Edmond-Gabow (EG) maximum weighted graph matching algorithm may be used, as described in: Gabow, H. N., "An Efficient Implementation of Edmonds' Algorithm for Maximum Matching on Graphs", Journal of the Association for Computing Machinery, vol. 23, no. 2, pages 221-234 (April 1976). The output of the EG algorithm is the determined connectivity. This output is compared against the actual connectivity described in the Swiss-Prot protein annotations to calculate the accuracy. The present invention discloses a novel and accurate method of computing the edge weights.

Figure 2:
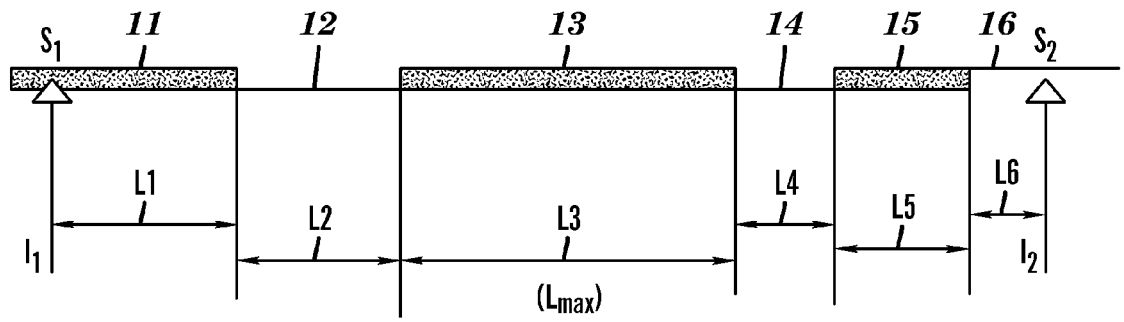
FIG. 2 illustrates a protein model, in accordance with embodiments of the present invention.

FIG. 2 illustrates a protein model, in accordance with embodiments of the present invention. In FIG. 2, $I_1$ and $I_2$ are cysteine position indexes at which the secondary structure unit is starting and ending, respectively. $S_1$ and $S_2$ denote the respective sulphur atoms of the cysteines at the position indexes $I_1$ and $I_2$. The thick lines 11, 13, and 15 represent rigid protein segments (e.g., alpha helixes and beta sheets) having lengths $L_1$, $L_3$, and $L_5$, respectively, between $I_1$ and $I_2$. The thin lines 12, 14, and 16 represent flexible protein segments (e.g., other secondary structures) having lengths $L_2$, $L_4$, and $L_6$, respectively, between $I_1$ and $I_2$. If $I_1$ or $I_2$ is positioned within a particular segment instead of at the end of the particular segment, then the length of said particular segment between $I_1$ and $I_2$ is the length of the portion of the particular segment between $I_1$ and $I_2$ instead of the whole length of the particular segment. In FIG. 2, the longest segment between $I_1$ and $I_2$ (generally denoted as $L_{max}$) is segment 13 having length $L_3$.

The weights assigned to the graph edges are calculated from a combination of weights derived from one or more of the following four weight sources (A, B, C, D).

A. Monte Carlo derived contact potential ($W_{mc}$)

B. Weights decreasing with increasing separation between cysteines in the chain ($W_d$)

C. Penalty for bonds between cysteines which are nearer than one to four residues in the chain (Proximity Penalty).

D. Penalty for bonds which cannot be formed without bending of Secondary Structure (Bending Penalty)

A. Monte Carlo Derived Contact Potential

The Monte Carlo derived contact potential ($W_{mc}$) that Fairselli and Casadio found to be best performing is based on the Edmonds-Gabow algorithm and Monte Carlo simulated annealing. See Piero Fariselli and Rita Casadio, "Prediction of disulphide Connectivity to proteins", BioInformatics, Vol 17 No. 10, Oxford University Press (2001). To illustrate, assume that the cysteine along with the four residues, two in each side of the chain, are in contact. For example if a first sulphur $S_1$ of a first cysteine at position $I_1$=5 in the chain and a second sulphur $S_2$ of a second cysteine at position $I_2$=21 in the chain are forming a disulphide bond, it is assumed that all the residues at positions 3, 4, 5, 6, and 7 are in contact with all the residues at 19, 20, 21, 22, and 23. Then the individual contact potentials are summed for all these cysteines to compute $W_{mc}$ as shown in Equation (3):

$$W_{mc} = \sum_i \sum_j W(R_i, R_j) \quad (3)$$

wherein $W(R_i, R_j)$ is the Monte Carlo calculated contact potential between cysteines Ri and Rj. $W(R_i, R_j)$ may be obtained by any method known to a person of ordinary skill in the art, such as from the values of $W(R_i, R_j)$ listed in Table 5 in Piero Fariselli and Rita Casadio, "Prediction of disulphide Connectivity to proteins", BioInformatics, Vol 17 No. 10, Oxford University Press (2001), a portion of which is depicted in FIG. 3. The Monte Carlo derived contact potential ($W_{mc}$) is the only factor used by Fairselli and Casadio to assign weights to graph edges.

Figure 4:
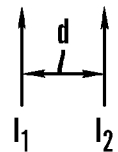
FIG. 4 provides an illustrative example for a sequence of amino acid residues, in accordance with embodiments of the present invention.

FIG. 4 provides an illustrative example for the sequence of amino acid residues FATCAPFGLCFK wherein $I_1=3$ and $I_2=9$, in accordance with embodiments of the present invention. Ri and Rj of Equation (3) denote cysteines associated with the residues "F", "A", "T", . . . of FATCAPFGLCFK. Given two residues on each side of $I_1$ and $I_2$ (i.e., the window size is 5), the windows for of $I_1$ and $I_2$ are ATCAP and GLFCK, respectively. Thus, $W_{mc}$ in Equation (5) is the sum of the following contact potentials: A-G (i.e., between A and G), A-L, A-C, A-F, A-K; T-G, T-L, T-C, T-F, T-K; C-G, C-L, C-C, C-F, C-K; A-G, A-L, A-C, A-F, A-K; P-G, P-L, P-C, P-F, P-K. These contact potential are the circled numbers in FIG. 3. For example, A-G=1.111, A-L=1.244, and C-F=0.619.

While the window size of 5 was used in the preceding example, the window size Z is variable; e.g. the window size Z is an odd positive integer of at least 3 (e.g., 3, 5, 7, 9, etc.). Generally, for a window size $Z_1$ and $Z_2$ with respect to the sequence indexes $I_1$ and $I_2$, there are $(Z_1-1)/2$ and $(Z_2-1)/2$ indexes on each side of the sequence indexes $I_1$ and $I_2$, respectively, wherein $Z_1$ and $Z_2$ are each an odd positive integer. The scope of the present invention includes embodiments in which $Z_1=Z_2$, as well as embodiments in which $Z_1$ and $Z_2$ are unequal.

B. Weights Decreasing with Increasing Separation Between Cysteines ($W_d$).

The following normal distribution with mean of zero and standard deviation ($\sigma$) illustrates an exponentially decreasing function $W_d$ that may be is used to assign the weights.

$$W_d = \frac{1}{\sigma\sqrt{2\pi}} e^{-(d^2/2\sigma^2)} \qquad (4)$$

$$d = \frac{|I_1 - I_2|}{100}$$

wherein $I_1$ and $I_2$ are the position indexes in the chain of the two cysteines, and d is a separation between $I_1$ and $I_2$ such that $d=|I_1-I_2|/100$. The standard deviation ($\sigma$) may be empirically determined. A representative value for $\sigma$ is 0.75, and a representative range for $\sigma$ is 0.50 to 0.90. Having the weights decrease with increasing separation between cysteines is based on the idea that disulphide bonding energy in proteins may not be going to the global minima of energy, but may be instead getting trapped in local energy minimas.

For the example of FIG. 4, the first cysteine has index $I_1=3$ in the sequence and second cysteine has index $I_2=9$ in the sequence and using $\theta=0.75$, then $$d = \frac{|3-9|}{100}$$
$$= 0.06$$
$$= 0.530$$

While the preceding discussion used a normal distribution to represent $W_d$ for illustrative purposes, the scope of the present invention generally defines $W_d$ to be a decreasing function of d; e.g., a function proportional to: $\exp(-d)$, $1/d^n$ (n being a positive real number exceeding 1), etc.

C. Penalty for Bonds Between Cysteines which are Nearer than One to Four Residues in the Chain (Proximity Penalty).

Each amino acid residue in the protein is indexed in ascending order starting at 0, (i.e., 1, 2, 3, etc.). Each index in a protein chain maps to a single amino acid residue.

The steric hindrance and excessive strain in the bonds may be preventing the proteins from folding.

$$W = \begin{cases} |I_1 - I_2| < M = 0 \\ |I_1 - I_2| \geq M = W \end{cases} \qquad (5)$$

$I_1$ and $I_2$ refers to indexes of sulphur atoms $S_1$ and $S_2$ of respective cysteines in the chain. If $|I_1-I_2|$ is less than M (wherein M=1 to 4), then the weight for that particular bond is set to 0, thereby overriding $W_{mc}$ and $W_d$. For the example of FIG. 4 with M=2, $I_1=3$ and $I_2=9$, then $|I_1-I_2|=|3-9|=6$ which is not less than 2, so that the proximity penalty is not applied. If on the other hand, $I_1=3$ and $I_2=4$ were to prevail, then $|I_1-I_2|=|3-4|=1$ which is less than 2, so that the proximity penalty would be applied and the weight would consequently be set equal to 0.

While the preceding example recites a penalty if the bonding between cysteines is less than 2 residues apart, the invention generally imposes this penalty if the bonding between cysteines is less than M residues apart, wherein M may be selected as an integer from 1 to 4.

D. Penalty for Bonds which cannot be Formed without Bending of Secondary Structure (Bending Penalty)

The bending penalty prevents bonding between the cysteines which require the bending of alpha helixes or beta sheets. Thus, the bending penalty is based on secondary structure constraints.

It is observed that secondary structure units such as alpha helixes and beta sheets don't bend. Mostly, the bending is in turns. Thus, proteins chain may be viewed as rigid alpha and beta structures connected by flexible turns. In this model, the criteria for two points in the chain to come together is that the longest single rigid segment between the two points should be shorter than sum of the lengths of the all other segments between the two points.

The criterion for this applying the bending penalty is given by Equation (6):

$$d_{12}^{min} = L_{max} - \sum_{i \neq max} L_i \qquad (6)$$

$$W = \begin{cases} d_{12}^{min} \leq 0 = W \\ d_{12}^{min} > 0 = 0 \end{cases}$$

where,
$d_{12}^{min}$ is the minimum possible distance between indexes $I_1$ and $I_2$ without bending alpha helixes or beta sheets, wherein $I_1$ and $I_2$ are indexes of sulphur atoms $S_1$ and $S_2$, respectively.
$L_i$=the length of a rigid or flexible segment between $I_1$ and $I_2$.
$L_{max}$=longest rigid segment between $I_1$ and $I_2$ If $d_{12}^{min}>0$, then the cysteine positions (or respective sulphur atom positions) at $I_1$ and $I_2$ will not be able to come together (i.e., touch each other) without bending of secondary structures (e.g., alpha helixes or beta sheets) at $I_1$ and $I_2$, which means that a first cysteine at $I_1$ and a second cysteine at $I_2$ cannot form a disulphide bond without bending rigid segments therebetween (i.e., the bond between respective sulphurs cannot form). Accordingly, if $d_{12}^{min}>0$, then the weight for that particular bond is set to 0, thereby overriding and $W_{mc}$ and $W_d$.

As an example, assume in FIG. 2 that $L_1=2$, $L_2=1$, $L_3=L_{max}=10$, $L_4=2$, $L_5=3$, and $L_6=1$. Then the sum of the lengths excluding $L_{max}$ is $L_1+L_2+L_4+L_5+L_6=9$ which is less than $L_{max}=10$. Therefore, $d_{12}^{min}>0$ for this example, which triggers the bending penalty and the weight for the bond between cysteine sulphurs at $I_1$ and $I_2$ is therefore set to 0.

As an alternate example, assume in FIG. 2 that $L_1=2$, $L_2=1$, $L_{max}=8$, $L_4=2$, $L_5=3$, and $L_6=1$. Then the sum of the lengths excluding $L_{max}$ is $L_1+L_2+L_4+L_5+L_6=9$ which is not less than $L_{max}=8$. Therefore, $d_{12}^{min}<0$ for this alternate example, the weight for the bond between cysteines at $I_1$ and $I_2$ is not subject to the bending penalty.

An overall function W to assign weights to graph edges may be given by:

$$W=aW_{mc}+bW_d \quad (7)$$

wherein a/b is in a range of 1.0 to 1.5. For example, a=100 and b=95 (i.e., a/b=1.05), wherein the weighting factors such as a=100 and b=95 may be obtained based on empirical results. The adjacency list representation of graphs obtained by applying all these constraints serves as input to the Edmond-Gabow maximum weighted graph matching algorithm to determine the connectivity. Other formulations for determining W include:

$$W=W_{mc} \quad (8)$$

$$W=W_d \quad (9)$$

For any of the Equations (7), (8), or (9, W may be subject to the penalty of Equation (5) and/or Equation (6).

Figure 5:
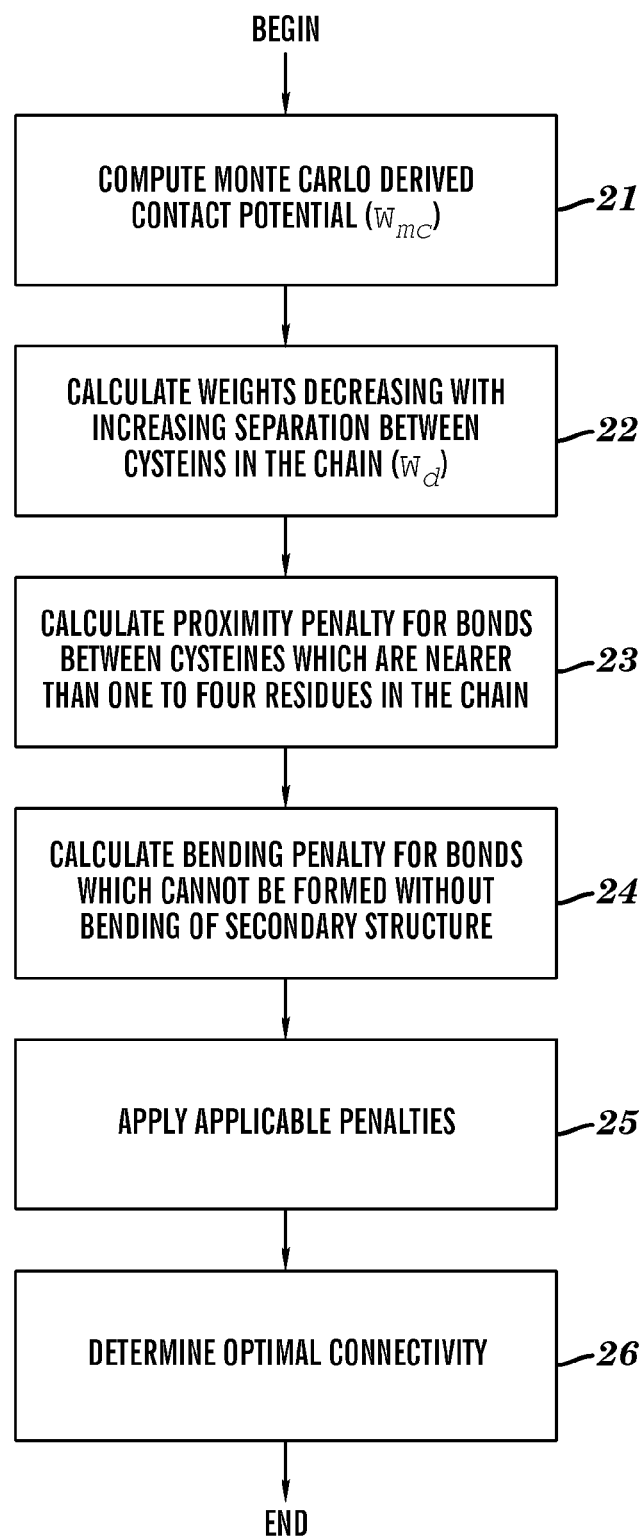
FIG. 5 is a high-level flow chart for determining the disulphide connectivity of proteins, in accordance with embodiments of the present invention.

FIG. 5 is a high-level flow chart comprising steps 21-26 for determining the disulphide connectivity of proteins, in accordance with embodiments of the present invention.

Step 21 computes a Monte Carlo derived contact potential ($W_{mc}$), as described supra in conjunction with Equation (3).

Step 22 calculates weights decreasing with increasing separation between cysteines in the chain ($W_d$), as described supra (e.g., see Equation (4)).

Step 23 calculates a proximity penalty for bonds between cysteines which are nearer than one to four residues in the chain, as described supra in conjunction with Equation (5).

Step 24 calculates a bending penalty for bonds which cannot be formed without bending of secondary structure (e.g., alpha helixes and/or beta sheets), as described supra in conjunction with Equation (6).

Step 25 applies the proximity penalty and/or bending penalty to W as applicable, as described supra.

Step 26 determines the optimum connectivity such as by using the Edmond-Gabow (EG) maximum weighted graph matching algorithm to maximize an objective function expressed as sum of the edge weights W to form the N disulphide bonds, as described supra.

Figure 6:
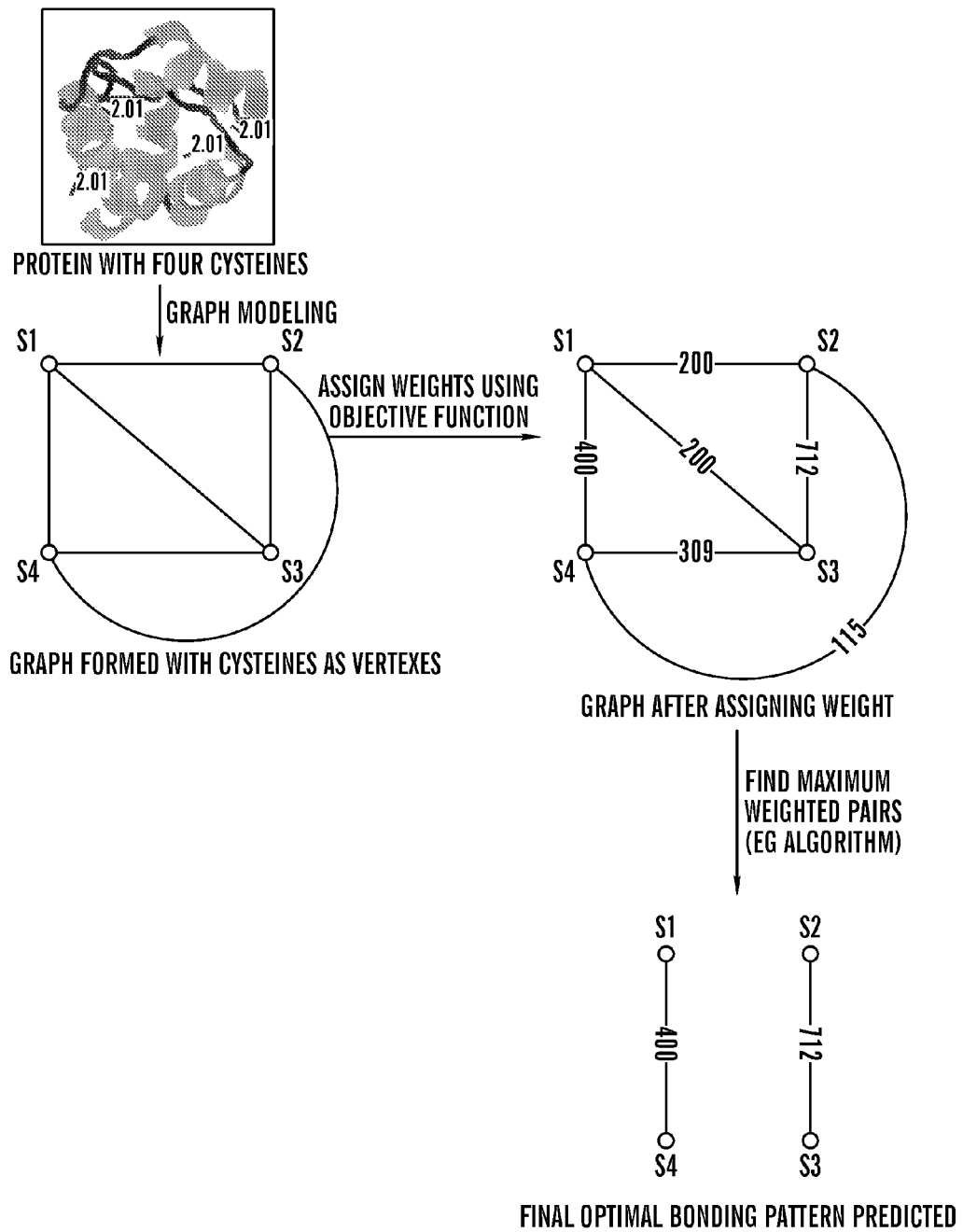
FIG. 6 depicts a process of modeling the proteins as a graph for an example in which an optimum connectivity is determined, in accordance with embodiments of the present invention.

FIG. 6 depicts a process of modeling the proteins as an undirected graph for an example in which an optimum connectivity is determined, in accordance with embodiments of the present invention. FIG. 6 depicts four sulphurs denoted as S1, S2, S3, and S4, with edge weights between the sulphurs in each pair of sulphurs shown to be: S1-S2 (200), S1-S3 (200), S!-S4 (400), S2-S3 (712), S2-S4 (115), and S3-S4 (309). The optimal connectivity is the pair of disulphide bonds in FIG. 6 whose sum of edge weights is a maximum, which turns out to be the S1-S4 and S2-S3 bonds whose sum of edge weights is 400+712=1112.

Figure 7A:
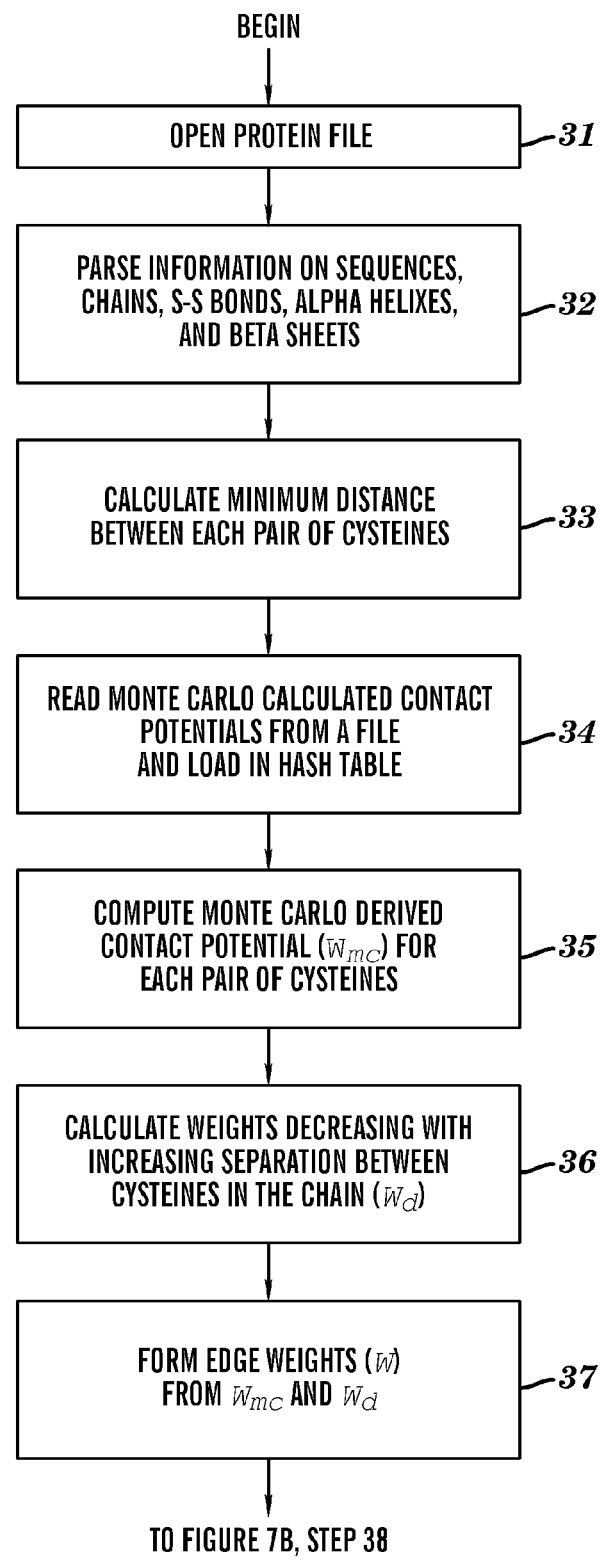
FIGS. 7A and 7B are collectively a detailed flow chart for determining and evaluating the disulphide connectivity of proteins, in accordance with embodiments of the present invention
Figure 7B:
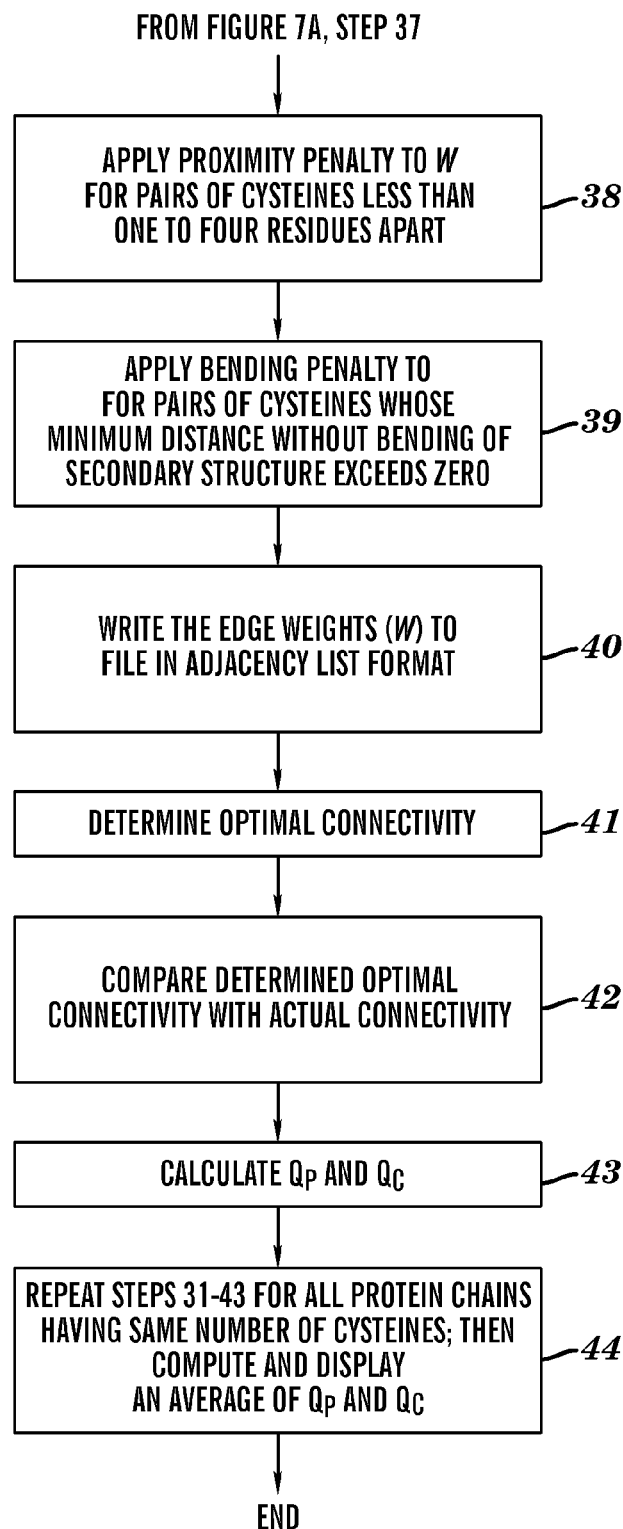

FIGS. 7A and 7B (collectively "FIG. 7") is a detailed flow chart comprising steps 31-44 for determining and evaluating the disulphide connectivity of proteins, in accordance with embodiments of the present invention.

Step 31 obtains the sequence information, disulphide bond information, and secondary structure information, places this information in a protein file, and opens this protein file for subsequent reading. This information serves as input for performing the connectivity determinations.

Step 32 parses the protein file of step 31 and loads the sequence, secondary structure, and disulphide bond information into appropriate data structures.

Step 33 calculates the minimum distance $d_{12}^{min}$ between each pair of cysteines without bending of secondary structure (e.g., alpha helixes and/or beta sheets), in accordance with Equation (6) using the secondary structure information. The calculated minimum distance is loaded to a hash table data structure.

Step 34 reads the Monte Carlo calculated contact potentials from a text file, by parsing the text file. The parsed Monte Carlo derived contact potential is stored in a hash table.

Step 35 computes the Monte Carlo derived contact potential ($W_{mc}$) for each pair of cysteines (see Equation (3)).

Step 36 calculates weights decreasing with increasing separation between cysteines in the chain ($W_d$) such as by use of Equation (4).

Step 37 forms the edge weights W such as by constructing a linearly weighted combination of $W_{mc}$ and $W_d$ as shown in Equation (7).

Steps 38 and 39 applies the proximity penalty and bending penalty to W, respectively, to the objective function resulting from step 37. Step 38 applies the proximity penalty to W for pairs of cysteines less than one to four residues apart, which sets the edge weight between the cysteines in the pair of cysteines equal to zero when the proximity penalty is applied. Step 39 applies the bending penalty to W for pairs of cysteines whose minimum distance exceeds zero, which sets the edge weight between the cysteines in the pair of cysteines equal to zero when the bending penalty is applied.

Step 40 writes the edge weights (W) obtained as a result of steps 37-39 into a text file in an adjacency list format to serve as input to the Edmond Gabow predicting algorithm.

Step 41 determines the optimal connectivity, such as by using the Edmond Gabow predicting algorithm.

Step 42 compares the determined optimal connectivity with the actual connectivity. The actual connectivity may be derived from the Swiss-Prot database as described supra.

Step 43 calculate Qc and Qp from Equations (1) and (2), respectively.

Step 44 repeats steps 31-43 for all protein chains having the same number of cysteines, followed by computing and displaying an average of $Q_P$ and $Q_C$.

Table 2 summarizes accuracy results of computation of disulphide connectivity by the present invention, using data from the Swiss-Prot database as described supra. The parameters EG, S, and D in Table 2 are defined as follows:

EG=simulated annealing (Monte Carlo) contact potential ($W_{mc}$) derived from Table 5 of Piero Fariselli and Rita Casadio, "Prediction of disulphide Connectivity to proteins", Bio-Informatics, Vol 17 No. 10, Oxford University Press (2001); a portion of Table 5 of Fariselli and Casadio is shown in FIG. 3.

D=constraints and weight based on separation between cysteines (proximity penalty; and $W_d$).

S=constraints based on secondary structure (bending penalty),

TABLE 2

| No. of S-S Bonds | No. Of Chains | $Q_P$(EG,S,D) | $Q_P$(EG) | $Q_C$(EG,S,D) | $Q_C$(EG) |
|---|---|---|---|---|---|
| 2 | 164 | 0.707 | 0.396 | 0.707 | 0.396 |
| 3 | 173 | 0.355 | 0.323 | 0.229 | 0.172 |
| 4 | 88 | 0.296 | 0.205 | 0.125 | 0.023 |
| 5 | 36 | 0.317 | 0.253 | 0.028 | 0.056 |
| 6 | 10 | 0.117 | 0.033 | 0.000 | 0.000 |

Table 2 shows that the calculation of $Q_P$ and $Q_C$ is more accurate by the method of the present invention ($Q_P$(EG,S,D) and $Q_C$(EG,S,D)) than the Fariselli and Casadio approach ($Q_P$(EG) and $Q_C$(EG)), with the exception of $Q_C$ for the case of 5 bonds and 36 chains.

Figure 8:
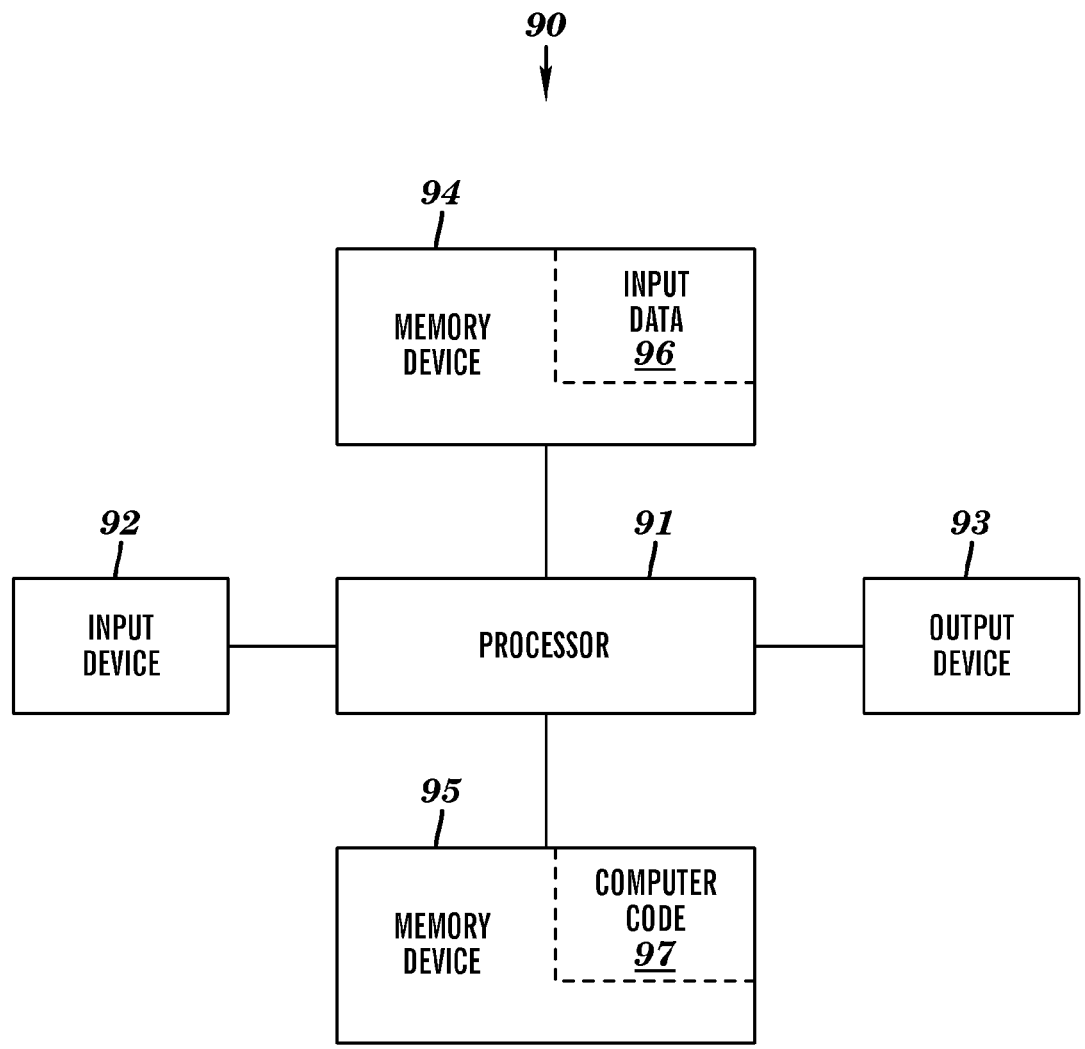
FIG. 8 illustrates a computer system used for determining disulphide bond connectivity in protein, in accordance with embodiments of the present invention.

FIG. 8 illustrates a computer system 90 used for determining disulphide bond connectivity in protein, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes an algorithm for determining disulphide bond connectivity in protein. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 8) may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device).

Thus the present invention discloses a process for deploying or integrating computing infrastructure, comprising integrating computer-readable code into the computer system 90, wherein the code in combination with the computer system 90 is capable of performing a method for determining disulphide bond connectivity in protein.

While FIG. 8 shows the computer system 90 as a particular configuration of hardware and software, any configuration of hardware and software, as would be known to a person of ordinary skill in the art, may be utilized for the purposes stated supra in conjunction with the particular computer system 90 of FIG. 8. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A process for integrating computing infrastructure, said process comprising integrating computer-readable code into a computing system, wherein the code in combination with the computing system is capable of performing a method for determining N disulphide bond connections in a protein comprising 2N bonded sulphur atoms, each sulphur atom being available for forming the N disulphide bond connections through use of an undirected graph having the 2N sulphur atoms as nodes and having an edge connecting each pair of nodes of the N nodes, each edge being a potential disulphide bond connection of the N disulphide bond connections to be determined, each sulphur atom of the 2N sulphur atoms being independently comprised by a cysteine of the protein, said cysteines being sequenced along a chain in the protein in accordance with an ordered list of position indexes 0, 1, 2, . . . , said N at least 2, said method comprising:

determining an edge weight W for each edge between a first sulphur atom $S_1$ of a cysteine positioned at a position index $I_1$ of the chain and a second sulphur atom $S_2$ of a cysteine positioned at a position index $I_2$ of the chain;

a processor of the computing system determining the N disulphide bond connections by optimizing an objective function formed from the determined edge weights W, wherein the objective function is a sum of the weights of the N disulphide bond connections, and wherein said optimizing comprises determining the N disulphide bond connections that maximize the objective function, and transmitting to an output device an identification of the determined N disulphide bond connections, wherein said determining the edge weights comprises:
ascertaining zero or more edges at which at least one penalty applies and at least one edge at which the at least one penalty does not apply;
setting the edge weight W equal to zero at each edge at which said ascertaining has ascertained that at the least one penalty applies; and
for each edge of the at least one edge at which said ascertaining has ascertained that the at least one penalty does not apply, calculating the edge weight W according to $W = W_{12}$ or $W = aW_{mc} + W_{12}$, wherein a and b are positive real numbers subject to a/b being in a range of 1.0 to 1.5,
wherein $W_{12}$ is a numerical value that a function $W_d$ of d has at $d = |I_1 - I_2|/100$,
wherein the function $W_d$ is a decreasing function of d,
wherein for each edge at which said calculating the edge weight W is according to $W = aW_{mc} + bW_{12}$, said calculating the edge weight W comprises determining $W_{mc} = \Sigma_i \Sigma_j W(R_i, R_j)$,
wherein $\Sigma_i \Sigma_j W(R_i, R_j)$ is a Monte Carlo derived contact potential between $R_i$ and $R_j$, wherein $R_i$ denotes a cysteine at the position indexes i defined by a window size $Z_1$ with respect to the position index $I_1$, wherein $R_j$ denotes a cysteine at the position indexes j defined by a window size $Z_2$ with respect to the position index $I_2$, and wherein $Z_1$ and $Z_2$ are each independently an odd integer of at least 3,
wherein the at least one penalty is selected from the group consisting of a proximity penalty, a bending penalty, and both the proximity penalty and the bending penalty,
wherein the proximity penalty applies if $|I_1 - I_2| < M$ such that M is an integer from 1 to 4, wherein the bending penalty applies if a minimum distance between $S_1$ and $S_2$ without bending of secondary structures of the protein between $S_1$ and $S_2$ is greater than zero.

2. The process of claim 1, wherein $W_d$ is a normal distribution of d characterized by a mean of zero and a standard deviation σ.

3. The process of claim 2, wherein σ is in a range of 0.50 to 0.90.

4. The process of claim 1, wherein said ascertaining has ascertained that the zero or more edges at which at the least one penalty applies consists of one or more edges at which at the least one penalty applies.

5. The process of claim 4, wherein the at least one penalty consists of both the proximity penalty and the bending penalty at an edge of the one or more edges at which at the least one penalty applies.

6. The process of claim 4, wherein the at least one penalty comprises the proximity penalty at an edge of the one or more edges at which at the least one penalty applies.

7. The process of claim 6, wherein M=2.

8. The process of claim 4, wherein at least one penalty comprises the bending penalty at an edge of the one or more edges at which at the least one penalty applies.

9. The process of claim 1, wherein said ascertaining has ascertained that the zero or more edges at which at least one penalty applies consists of zero edges at which at the least one penalty applies.

10. The process of claim 1, wherein $W_d$ is proportional to $\exp(-d)$ or is proportional to $1/d^n$ such that n is a positive real number exceeding 1.

11. The process of claim 1, wherein said calculating comprises calculating the edge weight W according to $W=W_{12}$.

12. The process of claim 1, wherein said calculating comprises calculating the edge weight W according to $W=aW_{mc}+bW_{12}$.

13. The process of claim 12, wherein a/b is about 100/95, and wherein $Z_1$ and $Z_2$ are each independently selected from the group consisting of 3, 5, and 7.

* * * * *